(12) United States Patent
Sakai et al.

(10) Patent No.: US 7,548,639 B2
(45) Date of Patent: Jun. 16, 2009

(54) DIAGNOSIS ASSISTING SYSTEM AND STORAGE MEDIUM HAVING DIAGNOSIS ASSISTING PROGRAM STORED THEREIN

(75) Inventors: Shuji Sakai, Fukuoka (JP); Naoki Sugiyama, Otawara (JP); Kenichi Niwa, Otawara (JP)

(73) Assignees: Kyushu TLO Company, Limited, Fukuoka-shi (JP); Toshiba Medical Systems Corporation, Otawara-shi (JP)

( * ) Notice: Subject to any disclaimer, the term of this patent is extended or adjusted under 35 U.S.C. 154(b) by 682 days.

(21) Appl. No.: 11/080,428

(22) Filed: Mar. 16, 2005

(65) Prior Publication Data

US 2005/0267337 A1 Dec. 1, 2005

(30) Foreign Application Priority Data

May 31, 2004 (JP) ............................. 2004-162204

(51) Int. Cl.
*G06K 9/00* (2006.01)
(52) U.S. Cl. ...................................... 382/128
(58) Field of Classification Search ................. 382/128; 600/300
See application file for complete search history.

(56) References Cited

U.S. PATENT DOCUMENTS 5,839,438 A * 11/1998 Graettinger et al. ......... 600/300

FOREIGN PATENT DOCUMENTS

| JP | 9-50470 | 2/1997 |
| JP | 2002-112986 | 4/2002 |
| JP | 2003-33327 | 2/2003 |
| JP | 2004-267273 | 9/2004 |

* cited by examiner

*Primary Examiner*—Tom Y Lu
(74) *Attorney, Agent, or Firm*—Oblon, Spivak, McClelland, Maier & Neustadt, P.C.

(57) ABSTRACT

A diagnosis assisting apparatus for assisting medical diagnosis that is carried out by executing a plurality of judgments relating to a medical abnormality which has appeared on an image in predetermined steps of execution, the apparatus includes a input unit configured to input a judgment result and a display unit configured to sequentially make display for prompting an input of the judgment result, based on the steps of execution and the judgment result inputted by the input unit.

13 Claims, 9 Drawing Sheets

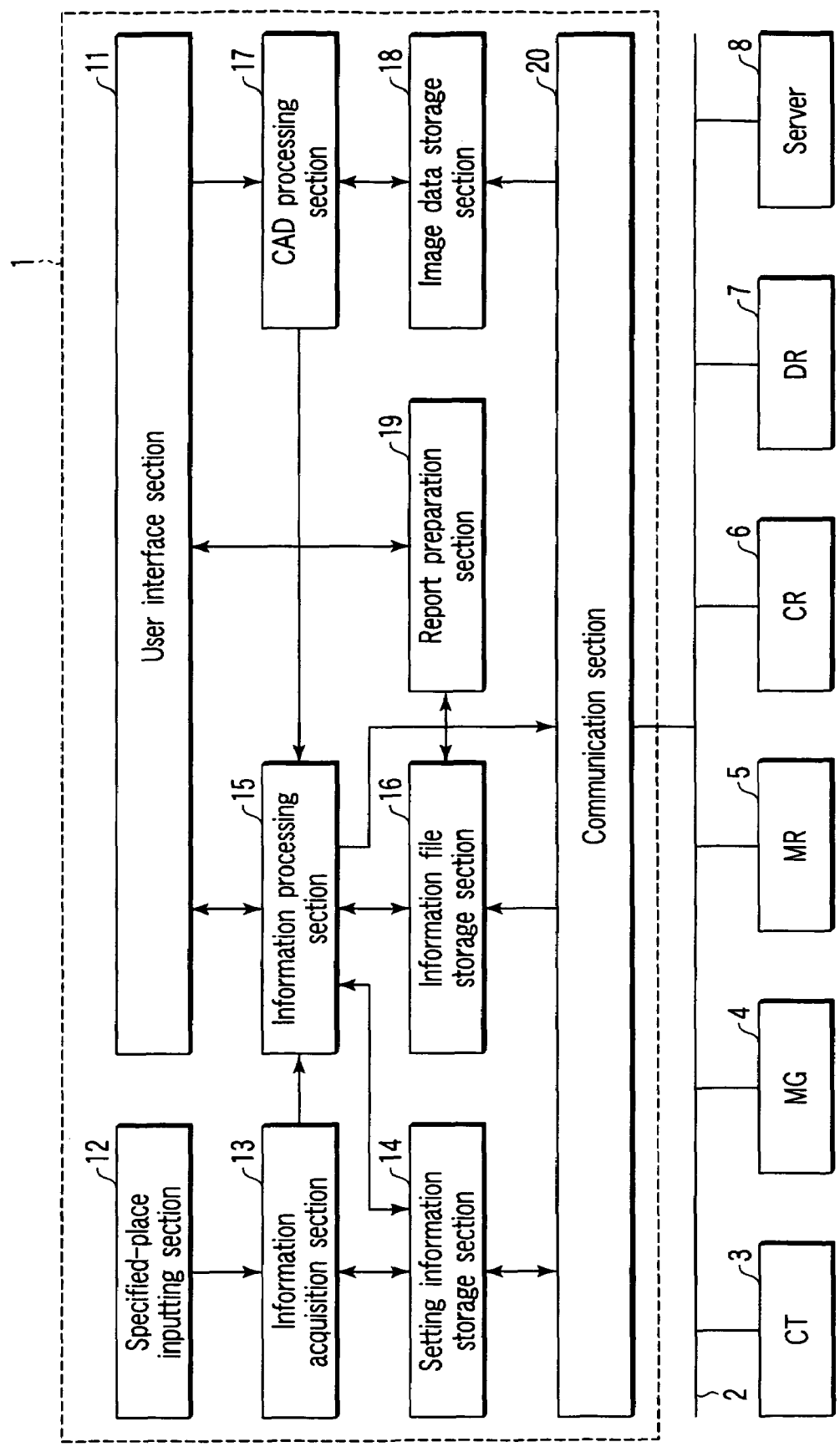
F I G. 1

| User name | Modality | Part for diagnostic reading | Step number | Tool type by its uses | Setting tool (or tools) | Criterion | Candidate information based on criterion |
|---|---|---|---|---|---|---|---|
| Doctor Smith | MG | Mammogram | 1 | Tool for determining growth or calcification | (1) Pixel value measuring tool (arrow) <br> (2) Pixel value measuring tool (rectangle) | 500 or more pixel values | When 500 or more pixel values exist, step number 3 is specified under the same condition for user, modality, and imaging part. If any different condition is established, step number 2 is specified |
| Doctor Smith | MG | Mammogram | 2 | ... | ... | ... | ... |
| Doctor Smith | MG | Mammogram | 3 | Tool for determining shape | (1) Pixel value measuring tool (specify) <br> (2) ...tool <br> (3) ...tool | ... | ... |
| ... | ... | ... | ... | | ... | ... | ... |
| Technician Kathy | CR | Leg | 1 | | (1) Pixel value measuring tool (specify) <br> (2) ...tool | 200 or more pixel values | |
| ... | ... | ... | ... | | ... | ... | |
| Technician Kathy | CR | Chest | 1 | | ... | | |
| ... | ... | ... | ... | | ... | | |

FIG. 2

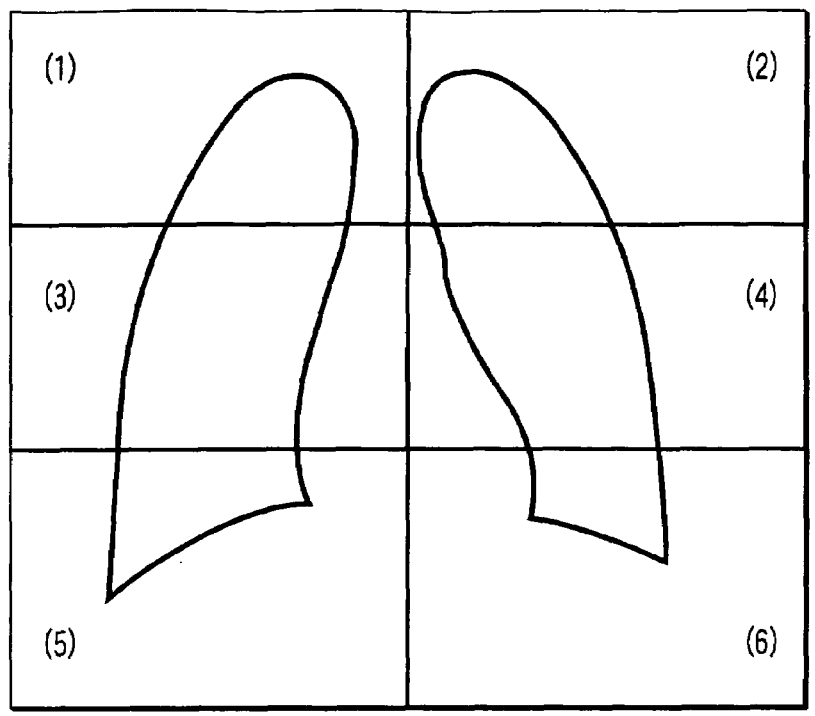
F I G. 8
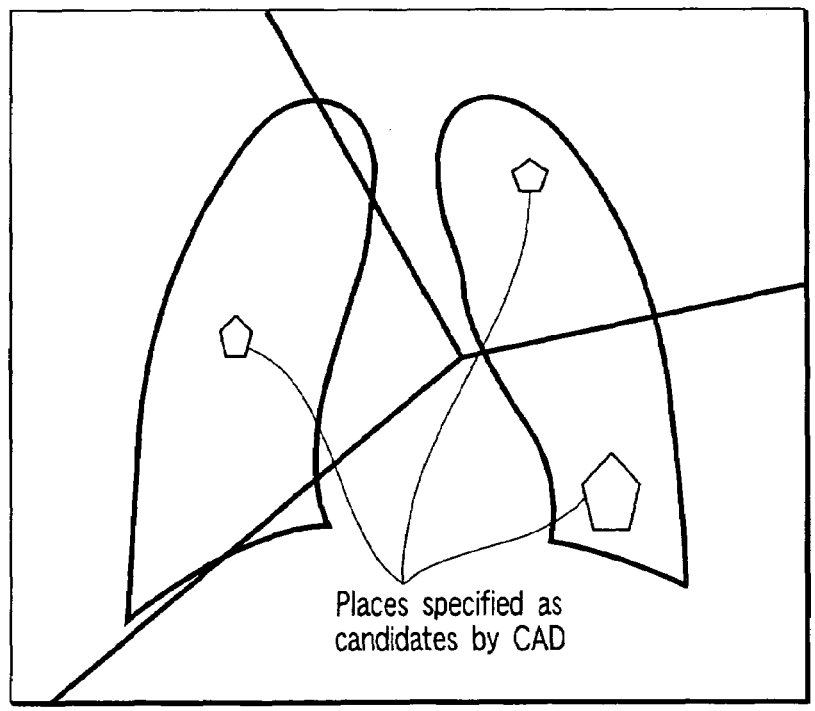
F I G. 9

| Divisional position information (three-dimensional information may exist) | Report entry characters | Input information<br>• Gaze of eye<br>• Shape<br>• Voice | Place to be moved on screen |
|---|---|---|---|
| Screen position information of (1) | Abnormality occurs with upper right field of lung | Gaze of eye | Upper left |
| Screen position information of (2) | Abnormality occurs with upper left field of lung | Gaze of eye | Upper right |
| ⋮ | ⋮ | ⋮ | ⋮ |

FIG. 10

```
<Diagnostic reading doctor>
  (John ^ Smith = RSD8)
  <Modality>
  (MMG)
  <Annotation coordinate position>
  (Circle : center (x = 51, y = 215) (radius 20)
  <Part>
  (Chest)
  <Disease>
  (Mass)
  <Conclusion>
  (Category 4 = 296.8)
  <Reason>
  (Is there central core ? = {Center : 20} Central core (-), This lesion has
  architectural distortion)
  (Margin diagnosis = Spicular (+))
  (Is fat contained ? = {Pixel value : 500} Mass not containing fat)
  Overlapping mammary glands or a mass ? = In the case where a mass is
  determined)
  (Determination of a mass or calcification = Mass)
```

FIG. 11

DIAGNOSIS ASSISTING SYSTEM AND STORAGE MEDIUM HAVING DIAGNOSIS ASSISTING PROGRAM STORED THEREIN

CROSS-REFERENCE TO RELATED APPLICATIONS

This application is based upon and claims the benefit of priority from prior Japanese Patent Application No. 2004-162204, filed May 31, 2004, the entire contents of which are incorporated herein by reference.

BACKGROUND OF THE INVENTION

1. Field of the Invention

The present invention relates to a diagnosis assisting apparatus and a storage medium having a diagnosis assisting program stored therein, for assisting medical diagnosis that is carried out based on an image acquired by a medical diagnostic apparatus.

2. Description of the Related Art

Conventionally, a graphical user interface (GUI) based viewer for assisting diagnostic reading, diagnosis, or explanation to a patient has been known. An interpreter or an observer such as a physician, especially radiologist, or obtains necessary information while using the viewer to carry out image processing or making a change for arrangement, display information and the like. In the viewer, image data acquired by the medical diagnostic apparatus and stored in an image server can be acquired and displayed as required. The medical examiner interprets the image displayed by the viewer.

In the case where there is a need for preparing and recording a report of a diagnosis result, the interpreter or the observer prepares such a report by utilizing a report viewer which is different from the above viewer or utilizing another software on the same viewer. In addition, in many facilities, a diagnosis result must be filled in recording paper by writing or be dictated to a transcriber without using the report viewer.

The GUI based viewer can change an image display mode, and however, the interpreter or the observer has carried out diagnostic reading directly.

In the case where diagnosis is carried out while preparing a report, the interpreter or the observer carries out diagnostic reading by using the GUI based viewer. Then, the interpreter or the observer must interrupt this diagnostic reading and prepare a report or fill the diagnosis result in the recording paper by utilizing a report terminal through some operating steps using a keyboard, a mouse, dictation, or the like. Therefore, with respect to a time required for the interpreter or the observer, an operating time for determining or keeping the result of diagnostic reading is added to a time for reading an actual image. In a system or the like in which a large amount of images per a unit time must be read, this time is relatively extended.

As described above, there has been a disadvantage that medical diagnosis based on an image becomes a considerable burden on the interpreter or the observer.

The associated prior application includes Japanese Patent Application No. 2003-58583 (Jpn. Pat. Appln. KOKAI Publication No. 2004-267273).

BRIEF SUMMARY OF THE INVENTION

In view of such circumstances, there has been a demand for assisting medical diagnosis based on an image in order to reduce a burden on an interpreter or an observer.

According to a first aspect of the present invention, there is provided a diagnosis assisting apparatus for assisting medical diagnosis that is carried out by executing a plurality of judgments relating to a medical abnormality which has appeared on an image in predetermined steps of execution, the apparatus comprising: a input unit configured to input a judgment result; and a display unit configured to sequentially make display for prompting an input of the judgment result, based on the steps of execution and the judgment result inputted by the input unit.

According to a second aspect of the present invention, there is provided a diagnosis assisting apparatus for assisting medical diagnosis that is carried out by executing a plurality of judgments relating to a medial abnormality which has appeared on an image in predetermined steps of execution, the apparatus comprising: a plurality of unit configured to acquire different items of information from the image; a judgment unit configured to sequentially make the judgment based on the steps of execution and the acquired information; and a display unit configured to display a history of the judgment result.

According to a third aspect of the present invention, there is provided a storage medium having stored therein a diagnosis assisting program which causes a computer to execute processing for assisting medical diagnosis that is carried out by executing a plurality of judgments relating to a medical abnormality which has appeared on an image in predetermined steps of execution, the diagnosis assisting program causing the computer to function as: a unit configured to input a judgment result; and a unit configured to sequentially make display for prompting an input of the judgment result based on the steps of execution and the judgment result.

According to a fourth aspect of the present invention, there is provided a storage medium having stored therein a diagnosis assisting program which causes a computer to execute processing for assisting medical diagnosis that is carried out by executing a plurality of judgments relating to a medical abnormality which has appeared on an image in predetermined steps of execution, the diagnosis assisting program causing the computer to function as: a plurality of unit configured to acquire different items of information from the image; a judgment unit configured to sequentially make the judgment based on the steps of execution and the acquired information; and a display unit configured to display a history of the judgment result by the judgment unit.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a diagram showing a configuration of a diagnosis assisting apparatus according to an embodiment of the present invention;

FIG. 2 shows an example of a setting information database;

FIG. 8 is a view showing an example of displaying an image of a chest to be divided into six frames by a template for chest;

FIG. 9 is a view showing an example of automatically dividing a differential image into a plurality of frames;

FIG. 10 shows an example of a chest setting database;

FIG. 11 is a view showing an example of structure report information; and

DETAILED DESCRIPTION OF THE INVENTION

Figure 3A:
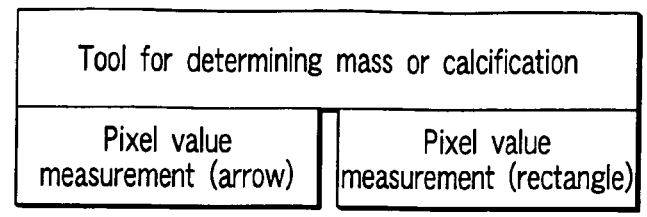
FIG. 3A and FIG. 3B are views each showing an example of displaying a tool list.

Hereinafter, an embodiment of the present invention will be described with reference to the accompanying drawings.

FIG. 1 is a diagram showing a configuration of a diagnosis assisting apparatus 1 according to the embodiment.

The diagnosis assisting apparatus 1 is connected to a local area network (LAN) 2 as shown in FIG. 1. Medical diagnostic apparatuses such as a computed tomography (CT) 3, a mammography (MG) 4, a magnetic resonance (MR) 5, a computed radiography (CR) 6, and a digital radiography (DR) 7 are properly connected to the LAN 2. Although not shown, as a medical diagnostic apparatus, there can be properly used: an endoscope, an ultrasonic diagnostic apparatus, a flat panel detector, an angiography apparatus, an electrocardiograph, an eyegrounds imaging apparatus, a digital microscope for cell diagnosis or pathological tissue diagnosis, or any other known apparatus. In addition, a server 8 is connected to the LAN 2. The server 8 stores image data acquired by the medical diagnostic apparatus. The server 8 sends the stored image data to the diagnosis assisting apparatus 1 in response to a request from the diagnosis assisting apparatus 1. The server 8 may store diagnosis-related information, order information, report information and the like without being limited to the image data.

As shown in FIG. 1, the diagnosis assisting apparatus 1 includes a user interface section 11, a specified-place inputting section 12, a information acquisition section 13, an setting information storage section 14, an information processing section 15, an information file storage section 16, computer aided diagnosis or detection (CAD) processing section 17, an image data storage section 18, a report preparation section 19, and a communication section 20.

The diagnosis assisting apparatus 1 can use, for example, a general-purpose server device or computer device as basic hardware. The specified-place inputting section 12, the information acquisition section 13, the information processing section 15, the CAD processing section 17, and the report preparation section 19 can be operated by causing a processor incorporated in the server device or the computer device to execute a program. The program may be installed on the server device or the computer device in advance. Alternatively, the program may be recorded on a removable recording medium such as a CD-ROM or be delivered to the server device or the computer device via a network, and then be installed on the server device or the computer apparatus. The setting information storage section 14, the information file storage section 16, and the image data storage section 18 can be operated by properly utilizing a storage device such as a memory or a hard disk unit incorporated in the server or the computer device; a storage device such as a memory or a hard disk unit externally provided to the server device or the computer device; and a removable storage medium such as an optical disk.

In the case where the user interface section 11 and the specified-place inputting section 12 are constructed on a GUI basis, the user interface section 11 and the specified-place inputting section 12 inputs an instruction in response to a signal output from an input device such as a mouse, a keyboard, a joystick, a pedal, or a pen. In addition, the user interface section 11 and the specified-place inputting section 12 can input an instruction supplied by the user's gaze, hand shape, voice or the like. The user interface section 11 causes a display device such as a liquid crystal display to display a variety of images in order to provide them to the user. The specified-place inputting section 12 informs a specified-place to the information acquisition section 13.

The information acquisition section 13 determines which condition and which tool is displayed in accordance with diagnostic reading procedures and acquires information based on the information stored in the setting information storage section 14.

The setting information storage section 14 stores a setting information database as shown in FIG. 2. The setting information database can be added, modified, and deleted by processing of the information processing section 15 in accordance with the user's instruction.

The information processing section 15 displays in a list or displays as a tree the information instructed from the information acquisition section 13. The information processing section 15 causes the user to, if the information is displayed in a list, select the list.

The information file storage section 16 stores viewer-related information, diagnosis-related information, order information, report information, and the like.

The CAD processing section 17 processes image data as a temporal subtraction image (the current and previous images are required under the same modality and the same condition), a nodule detection image, or the like in accordance with the user's instruction. Further, the CAD processing section 17 can determine a problematic place. When some candidates are listed, the CAD processing section 17 carries out image division in order to select any of them. Of course, the image data may be transmitted to the information processing section 15 intact without carrying out such processing in accordance with the user's instruction.

The image data storage section 18 stores image data acquired from the server 8.

The report preparation section 19 prepares report information relating to diagnosis carried out by utilizing the diagnosis assisting apparatus 1.

The communication section 20 makes communication via the LAN 2.

Now, an operation of the thus configured diagnosis assisting apparatus 1 will be described here.

The diagnosis assisting apparatus 1 has the following functions.

[1] Function of Setting a Tool on a Part by Part Basis for Diagnostic Reading

For example, in mammogram diagnostic reading, a mass, a calcification, or others is first determined. The tools utilized for that purpose (for example, a tool for measuring a pixel value) are described as "setting tools" in the setting information database. If an instruction for adding, modifying, or deleting these setting tools has been inputted by the user interface section 11, the information processing section 15 updates the setting information database in accordance with this instruction. In this manner, the user can register an arbitrary tool as a setting tool.

Figure 3B:
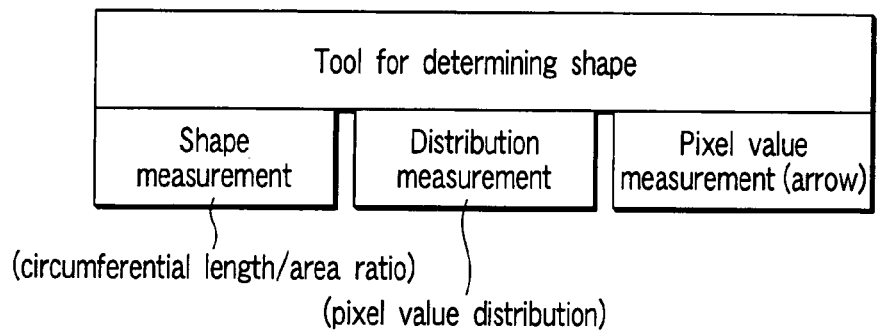

Specifically, in the case where doctor Smith selects mammogram diagnostic reading or in the case where mammogram diagnostic reading is automatically selected by a modality or a part for diagnostic reading, when a first judgment should be made, i.e., when step number is "1", an "image value measuring tool (arrow)" and a "pixel value measuring tool (rectangle)" are registered as setting tools, as shown in FIG. 2. Thus, the image as shown in FIG. 3A is displayed in the vicinity of a cursor. If it is necessary to determine the calcification is benign or malignant and the step therefore advances, the image displayed changes to an image indicating a setting tool that accords to new procedures, as illustrated in, for example, FIG. 3B. The setting tools in a list of all tools may be displayed so as to be determined by their positions or density/attenuation.

In the case where the thus displayed image has been clicked, a tool corresponding to the clicked place is activated, and information such as a pixel value, is acquired from the clicked image by means of this tool. In this manner, the user can easily select a tool.

[2] Candidate List Display Function

For example, in mammogram diagnostic reading, diagnosis is carried out by making a judgment of "discrimination of mass, calcification, or others" or "judgment of overlapping of mammary glands or a mass" in predetermined diagnosis procedures. The information processing section 15 sequentially displays a judgment option in accordance with the diagnostic procedures while the user inputs one's specified judgment result.

Figure 4:
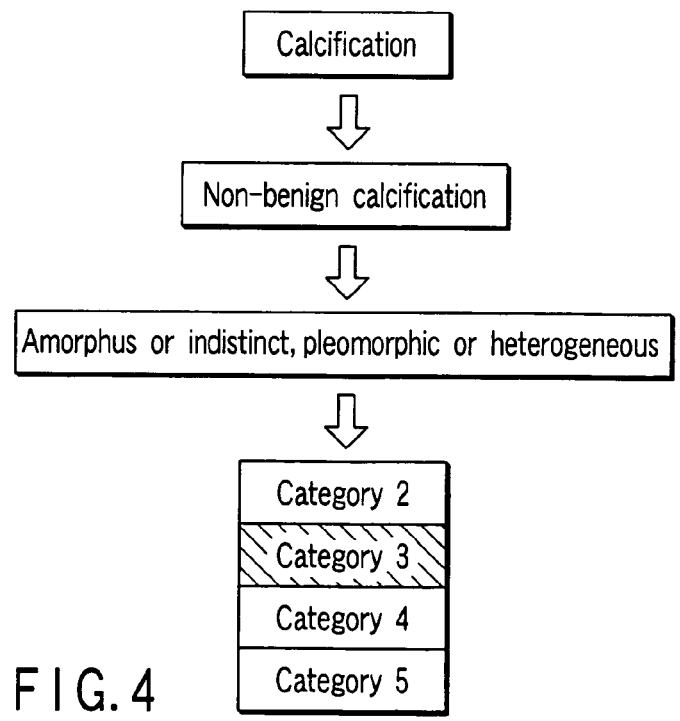
FIG. 4 is a view showing an example of displaying an image which shows a history of a diagnosis result derived by a user's judgment.

The information processing section 15 displays a history of a diagnosis result derived by each judgment by using, for example, an image as shown in FIG. 4. In FIG. 4, in mammogram diagnostic reading, there is shown an example in which category 3 on BI-RADS (Breast Imaging Reporting and Data System) classification is derived as a diagnosis result based on judgments of:

(1) Calcification has been determined by judgment of mass or calcification;

(2) It has been determined that the calcification is not clearly benign by a judgment of whether calcification is typically benign or not; and (3) The calcification has been determined to amorphus/indistinct, obscure shape, and clustered as a judgment of its shape and distribution.

Figure 5:
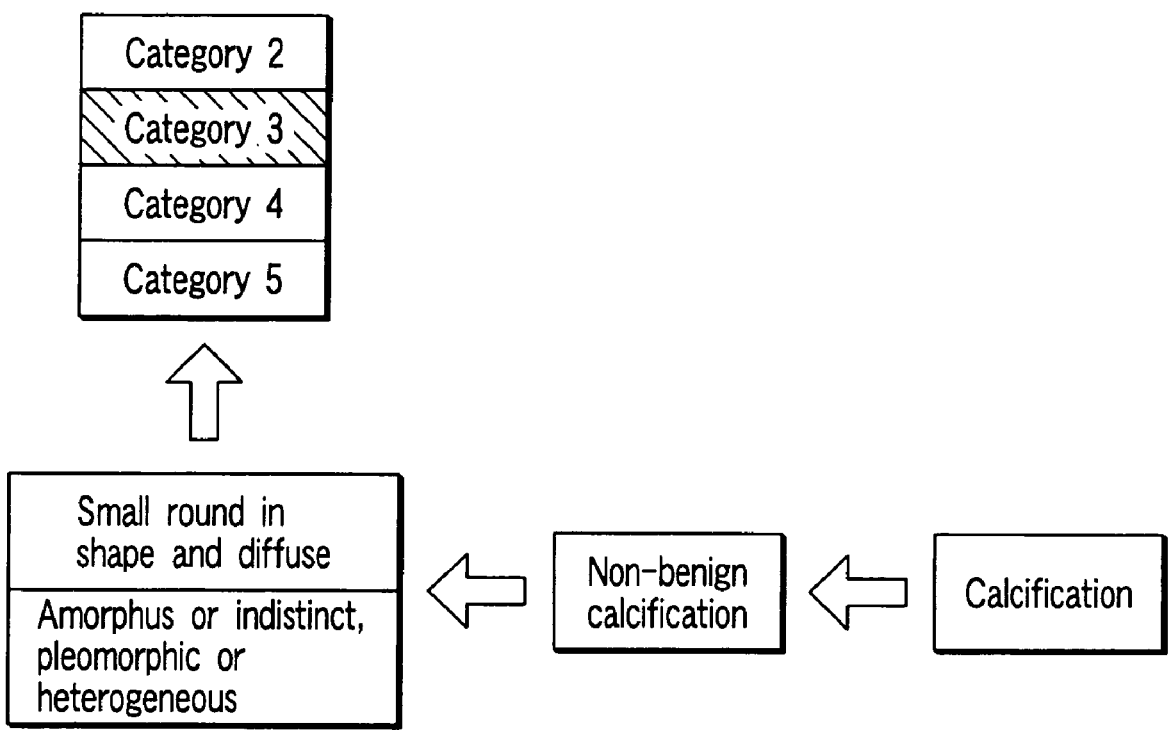
FIG. 5 is a view showing an example of displaying an image which shows a history of judgment for deriving a specified diagnosis result.

In addition, after a list of items which can be derived as a diagnosis result has been presented, in the case where the user has selected one of these items, the information processing section 15 determines a judgment and a history for deriving this selected item as a diagnosis result, and displays an image as shown in FIG. 5, for example. In FIG. 5, there is shown an example in which category 2 on BI-RADS classification has been selected as a diagnosis result of mammogram diagnostic reading. The figure also shows that the selected category 2 is derived as a diagnosis result by judgments of:

(1) Calcification has been determined by a judgment of mass or calcification;

(2) It has been determined that the calcification is not clearly benign by a judgment of whether the calcification is clearly benign or not; and (3) It has been determined that the calcification is small and round in shape and diffusible or amorphus/indistinct, obscure shape, and diffusible as a result of its shape and distribution.

If the user has instructs a change of any judgment result in the image shown in FIG. 4 or 5, the information processing section 15 restarts display of options and input of the judgment result specified by the user from the step which corresponds to the judgment result.

With this function, the diagnosis procedures are guided by a display, thus making it possible for the user to easily carry out diagnosis in accordance with this guidance.

[3] Function for Automatic Determination of a Plurality of Options in List and Displaying Determination Reason The information processing section 15 automatically executes each judgment in the diagnosis procedures. Then, the information processing section 15, for example, as shown in FIG. 6 or 7, displays an image showing options in each judgment, a history of a result in each judgment, and referenced information in each judgment (such as a numeric value acquired by a tool) and reason(s) referred to in each judgment.

Figure 6:
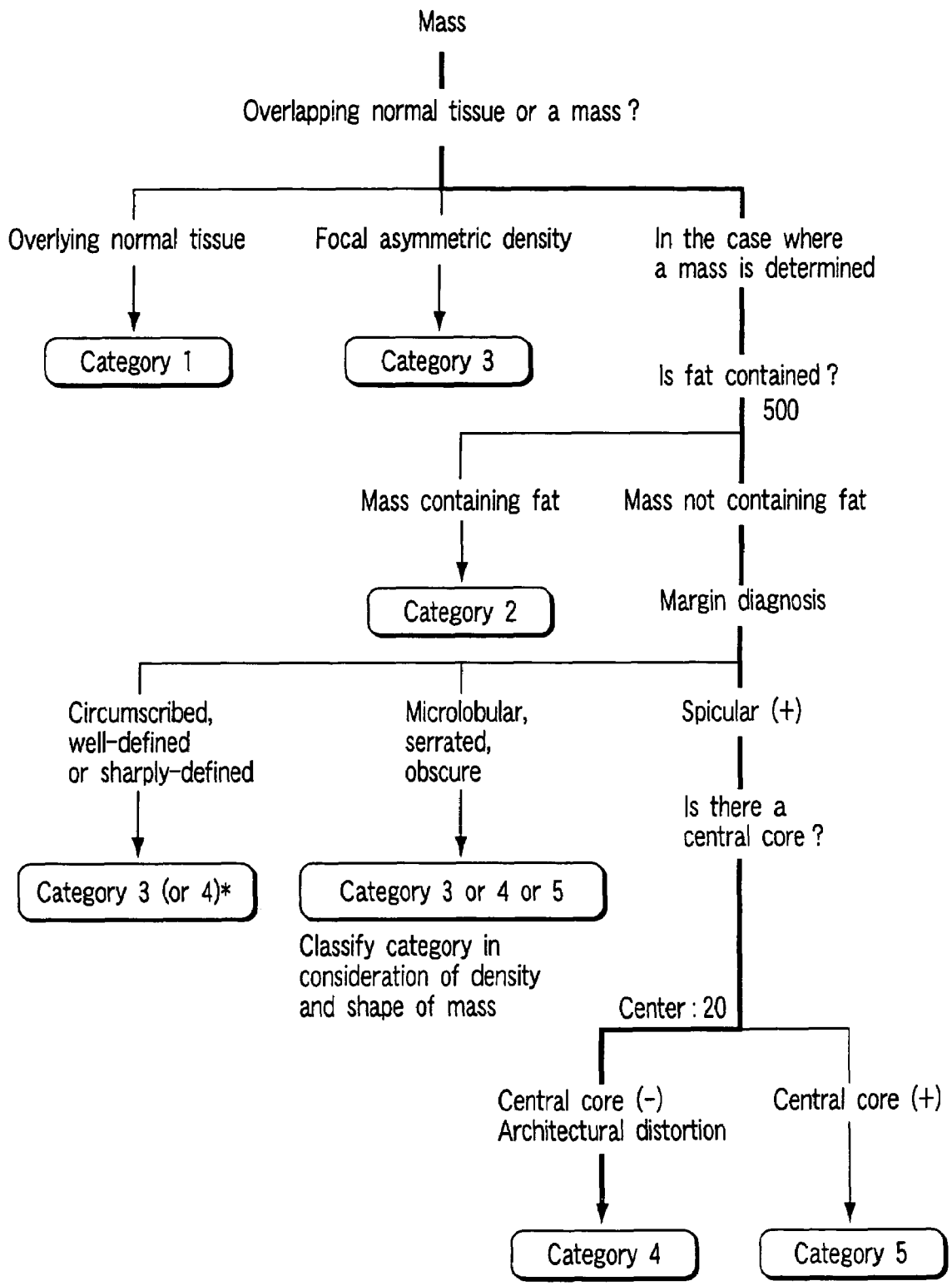
FIG. 6 is a view showing an example of displaying an image which shows a result obtained by automatically executing each judgment in diagnosis procedures.
Figure 7:
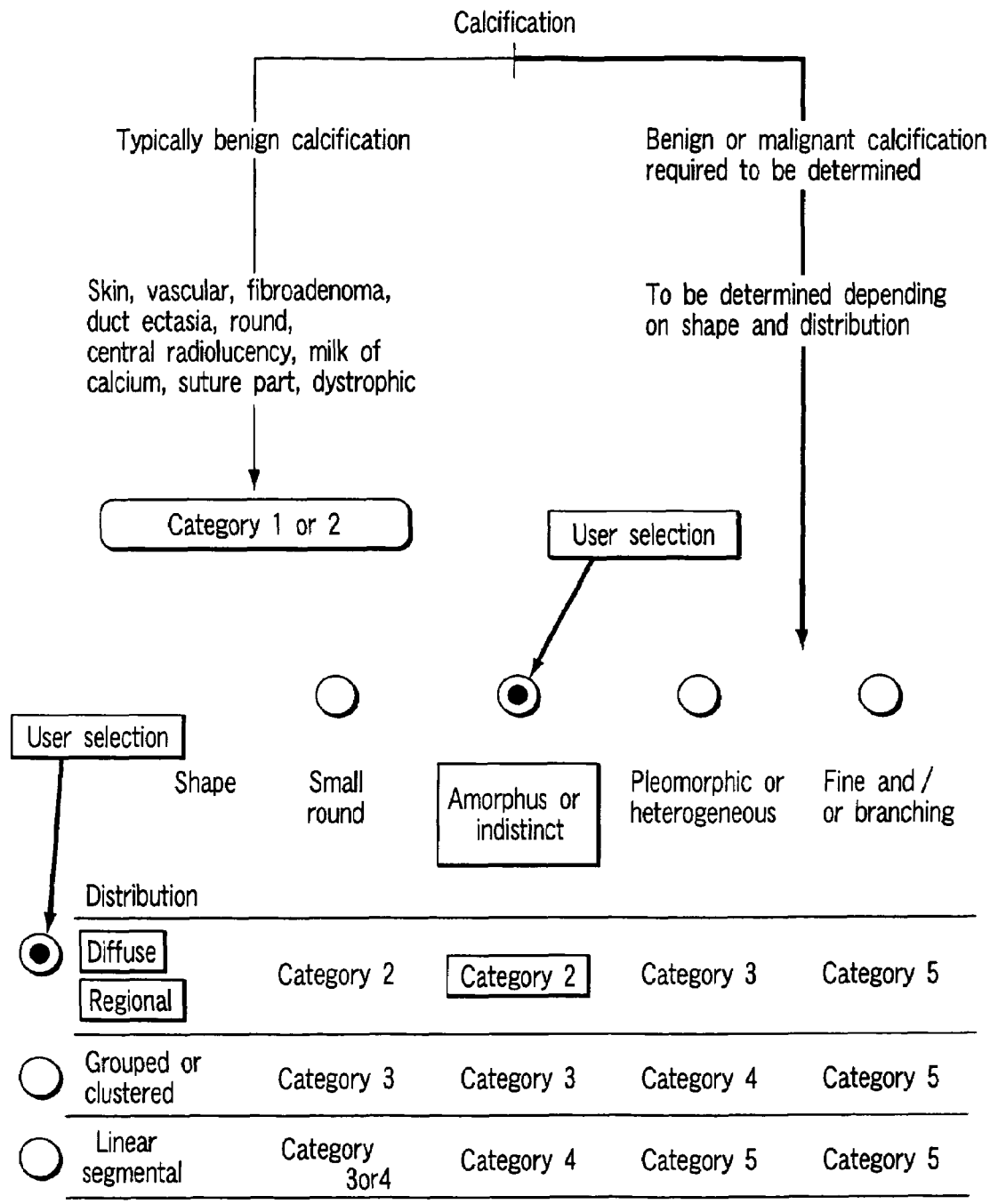
FIG. 7 is a view showing an example of displaying an image which shows a result obtained by automatically executing each judgment in diagnosis procedures.

FIG. 6 shows the whole diagnosis procedures relating to a mass in a tree shape and shows an automatically determined history by the thick line. In addition, in judgment of whether or not a fat is included, the figure shows that a numeric value "500" acquired by a tool has been referenced.

In judgment in which automatic determination is difficult, the user is presented with options, thereby prompting the user to make a judgment. For example, in FIG. 7, it is difficult to automatically make a judgment of the shape and distribution relating to calcification. Thus, the options as shown in FIG. 7 are displayed, thereby prompting the user to make this judgment.

With this function, a diagnosis result can be obtained even without the user making a judgment. Then, the judgment history is displayed, thus making it possible to check the history of judgment of the above diagnosis result based on this display. The validity of the diagnosis result can be verified. Further, judgment can be restarted from an arbitrary step. Thus, in the case where automatic judgment has been improper, the user's judgment can be easily restarted from the step only.

[4] Template Function for Determining Simply Specified Part on a Part by Part Basis for Diagnostic Reading After a template having indicated divisional frames set on a part by part basis has been set, when the part is read as an image, partial specification is accepted in accordance with the template. FIG. 8 is a view showing an example in which an image of a chest is displayed to be divided into six frames by a template for chest.

In addition, in the case where the current image and the past image coexist, when a differential image after elapse of time (applicable to nodule candidates or a processed image in CAD or edging) is displayed, if two changes occur with the image, the displayed image is divided as shown in, for example, FIG. 9, making it easy to select places in which the above changes occur. FIG. 9 shows an example in which, with intermediate points of three candidates being start points, an image has been divided into three frames in accordance with a segment of line passing though an intermediate point of two of the candidates.

For example, after the template of FIG. 8 has been applied, when an image of the chest is displayed, assume that the viewing position inputted by the specified-place inputting section 12 is within the range of "1" shown in FIG. 8. In this case, information indicating that "abnormality occurs with the upper right field of the lung" can be obtained by referring to the setting database as shown in FIG. 10. However, in the case where a plurality of candidates exists in one selected region, a list of these candidates is displayed, whereby the user may select one of these candidates.

A template is arbitrarily registered or changed according to the user's specification.

Also, a template may not be set in a two-dimensional manner as shown in the above-described example or may be set in a three-dimensional manner. In this case, volume information having depth may be used as divisional position information.

With this function, an imaging region targeted for diagnosis can be easily narrowed.

[5] Function for Adjusting Image Display Position

When diagnosis starts, the information processing section 15 uses almost or all of the display regions of a display device to display an image acquired by a medical diagnosis apparatus. If one region is specified by utilizing the template function, the information processing section 15 determines a place to be moved by referring to, for example, the setting database shown in FIG. 10. The information processing section 15 then moves the selected region to the determined place, and defines another region of the display regions of the display device as another image display region. Specifically, if region "1" shown in FIG. 8 has been selected, the place to be moved from that shown in FIG. 10 is the upper left. Thus, the image in region "1" shown in FIG. 8 is moved to the upper left of the display region of the display device. Then, image display in regions "2" to "6" shown in FIG. 8 terminates.

With this function, it becomes possible to make an efficient display by efficiently utilizing a limited display region of the display device.

[6] Function for Automatic Preparation of Report

The information processing section 15 stores: a judgment result inputted by a user in each judgment; a determination result obtained by automatically determination; information acquired by a tool; and the like in the information file storage section 16, thereby preparing structured report information relating to each diagnosis (structured report information). For example, with respect to the diagnosis in which the result as shown in FIG. 6 has been obtained, the structured report information as shown in FIG. 11 is prepared.

Figure 12:
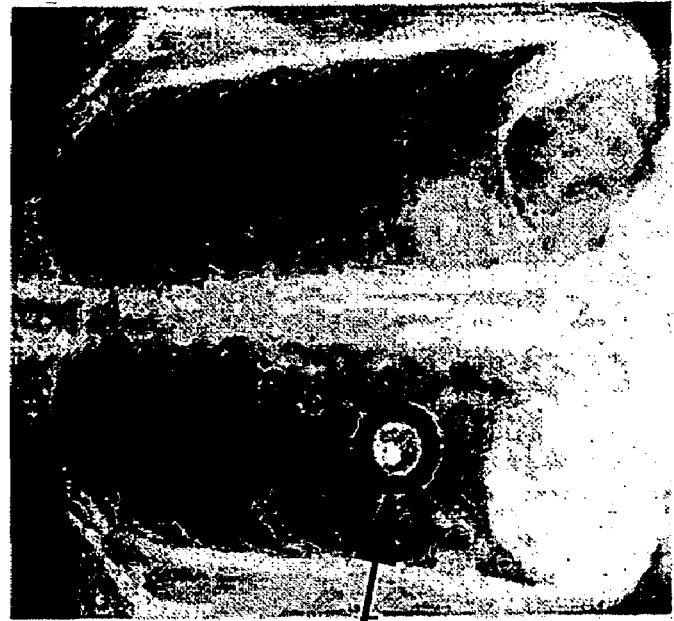
FIG. 12 is a view showing an example of a report.

The report preparation section 19 compiles: information included in the above-described structured report information; and an image used for diagnosis, in a predetermined layout, thereby preparing report information indicating a report as shown in FIG. 12, for example.

With this function, there is no need for the user to separately prepare a report by using a report viewer.

In addition, the thus prepared structured report information may be displayed together with the past structured report information relating to the same case of diseases as required. Doing so makes it possible to easily make a reference to the past diagnosis results of the same case of diseases and makes it possible to efficiently use comparative diagnostic reading.

Further, a function for making the diagnosis result coincident with general-purpose diagnosis classification such as an International Classification of Diseases (ICD-10) code may be provided. With this function, the diagnosis result can be efficiently used in the diagnosis and procedure combinations.

According to the embodiment described above, the above various kinds of functions support the work of the user, respectively. This makes it possible to reduce a burden on the user. At the same time, this makes it possible to reduce a burden on those involved in storage and management of the diagnosis results.

The embodiment enables a various kinds of modifications as follow.

All of the various functions described above may not always be provided, and a diagnosis assisting apparatus which eliminates some of these functions can be provided.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A diagnosis assisting apparatus for assisting medical diagnosis that is carried out by executing a plurality of judgments relating to a medical abnormality which has appeared on an image in predetermined steps of execution, the apparatus comprising:
    a input unit configured to input each result of the plurality of judgments;
    a display unit configured to selectively display a plurality of tools used to acquire, from the image, information to be referred to for the plurality of judgments, and configured to sequentially provide a display for prompting an input of the results of the plurality of judgments by sequentially changing the tools to be displayed based on the predetermined steps of execution and a state of the input of each result of the plurality of judgments by the input unit; and
    a determination unit configured to determine a result of the medical diagnosis, based on each of the results of the plurality of judgments input by the input unit.

2. The diagnosis assisting apparatus according to claim 1, further comprising a unit configured to compile the judgment results, thereby preparing a report.

3. The diagnosis assisting apparatus according to claim 1, further comprising a unit configured to select one of a plurality of steps of execution based on at least one item of information such as user identification information, modality, and an imaging part,
    wherein the display unit refers to the selected steps of execution.

4. A diagnosis assisting apparatus for assisting medical diagnosis that is carried out by executing a plurality of judgments relating to a medial abnormality which has appeared on an image in predetermined steps of execution, the apparatus comprising:
    an input unit configured to input each result of the plurality of judgments;
    a first display unit configured to selectively display a plurality of tools used to acquire from the image, information to be referred to for the plurality of judgments, and configured to sequentially provide a display for prompting an input of the results of the plurality of judgments by sequentially changing the tools displayed based on the predetermined steps of execution and a state of the input of each result of the plurality of judgments by the input unit;
    a determination unit configured to determine a result of the medical diagnosis, based on each of the results of the plurality judgments input by the input unit; and a second display unit configured to display a history of those results of the plurality of judgments which have been used to determine the result of the medical diagnosis.

5. The diagnosis assisting apparatus according to claim 4, further comprising a unit configured to compile the judgment results, thereby preparing a report.

6. The diagnosis assisting apparatus according to claim 4, further comprising a unit configured to select one of a plurality of steps of execution based on at least one item of information such as user identification information, modality, and an imaging part,
wherein the first display unit refers to the selected steps of execution.

7. The diagnosis assisting apparatus according to claim 4, wherein the determination unit includes at least one of a unit configured to make a determination of a mass and a unit configured to make a determination of calcification.

8. A computer-readable storage medium having stored therein a diagnosis assisting program which causes a computer to execute processing for assisting medical diagnosis that is carried out by executing a plurality of judgments relating to a medical abnormality which has appeared on an image in predetermined steps of execution, the diagnosis assisting program causing the computer to function as:
an input unit configured to input each result of the plurality of judgments; and
a display unit configured to selectively display a plurality of tools used to acquire, from the image, information to be referred to for the plurality of judgments, and configured to sequentially provide a display for prompting an input of the results of the plurality of judgments by sequentially changing the tools displayed based on the predetermined steps of execution and a state of the input of each result of the plurality of judgments by the input unit; and
a determination unit configured to determine a result of the medical diagnosis, based on each of the results of the judgments input by the input unit.

9. The computer-readable storage medium according to claim 8, having stored therein the diagnosis assisting program which causes the computer to further function as a unit configured to allocate the judgment result and preparing a report.

10. The computer readable storage medium according to claim 8, having stored therein the diagnosis assisting program which causes the computer to further function as a unit configured to select one of a plurality of steps of execution based on at least one item of information such as user identification information, modality, and an imaging part; and which causes the display unit to function as a unit configured to refer to the selected steps of execution.

11. A computer-readable medium having stored therein a diagnosis assisting program which causes a computer to execute processing for assisting medical diagnosis that is carried out by executing a plurality of judgments relating to a medical abnormality which has appeared on an image in predetermined steps of execution, the diagnosis assisting program causing the computer to function as a diagnosis assisting apparatus comprising:
an input unit configured to input each of results of the judgments;
a display unit configured to selectively display a plurality of tools used to acquire, from the image, information to be referred to for the judgments, and configured to sequentially make display for prompting an input of the results of the judgments by sequentially changing the tools to display, based on the predetermined steps of execution and a state of the input of each result of the judgments by the input unit;
a determination unit configured to determine a result of the medical diagnosis, based on each of the results of the judgments input by the input unit; and
a second display unit configured to display a history of those results of the plurality of judgments which have been used to determine the result of the medical diagnosis.

12. The computer-readable medium according to claim 11, having stored therein the diagnosis assisting program which causes the computer to further function as a unit configured to allocate the judgment result and preparing a report.

13. The computer-readable medium according to claim 12, having stored therein the diagnosis assisting program which causes the computer to further function as a unit configured to select one of a plurality of steps of execution based on at least one item of information such as user identification information, modality, and an imaging part; and which causes the first display unit to refer to the selected steps of execution.

* * * * *